(12) United States Patent
Iyoda et al.

(10) Patent No.: US 9,074,227 B2
(45) Date of Patent: Jul. 7, 2015

(54) HELICAL FINE STRUCTURE, METHOD FOR PRODUCING THE SAME, AND ELECTRIC-WAVE SHIELD OR ABSORBER USING THE HELICAL FINE STRUCTURE

(75) Inventors: Tomokazu Iyoda, Tokyo (JP); Kaori Ito, Tokyo (JP); Atsushi Yamada, Tokyo (JP)

(73) Assignees: TOKYO INSTITUTE OF TECHNOLOGY, Tokyo (JP); SUMITOMO METAL MINING CO., LTD., Tokyo (JP)

( * ) Notice: Subject to any disclaimer, the term of this patent is extended or adjusted under 35 U.S.C. 154(b) by 235 days.

(21) Appl. No.: 13/262,024

(22) PCT Filed: Apr. 19, 2010

(86) PCT No.: PCT/JP2010/057306
§ 371 (c)(1),
(2), (4) Date: Oct. 11, 2011

(87) PCT Pub. No.: WO2010/123130
PCT Pub. Date: Oct. 28, 2010

(65) Prior Publication Data
US 2012/0031663 A1 Feb. 9, 2012

(30) Foreign Application Priority Data
Apr. 22, 2009 (JP) ................... 2009-103681

(51) Int. Cl.
| | | |
|---|---|---|
| C12N 13/00 | (2006.01) | |
| C12N 1/00 | (2006.01) | |
| C12N 1/12 | (2006.01) | |
| A01H 1/02 | (2006.01) | |
| C12P 1/04 | (2006.01) | |
| H05K 9/00 | (2006.01) | |

(52) U.S. Cl.
CPC .............. *C12P 1/04* (2013.01); *Y10T 428/2925* (2015.01); *Y10T 428/2924* (2015.01); *C12N 1/12* (2013.01); *H05K 9/009* (2013.01); *H05K 9/0081* (2013.01)

(58) Field of Classification Search
CPC .............. C12N 1/00; C12N 1/02; C12N 1/04; C12N 1/12; C23C 2/00; C23C 22/00; C23C 18/04; C23C 18/08; C23C 26/00; B82Y 40/00; C01G 1/00; C25D 1/00
USPC ........... 530/820; 428/357, 689, 371; 427/212, 427/214, 487, 121, 100, 123, 58, 126.1; 435/174
See application file for complete search history.

(56) References Cited

U.S. PATENT DOCUMENTS

2005/0013759 A1* 1/2005 Grow .......................... 423/263

FOREIGN PATENT DOCUMENTS

| JP | 2000-27072 | 1/2000 |
| JP | 2009-221149 A1 | 10/2009 |

OTHER PUBLICATIONS

Cai et al. 2010 (published online Apr. 1, 2010; Fabrication and Dielectric Properties of Soft-core Helical Particles Using *Spirulina platensis* as Templates, Advances in Natural Science, 3(2):93-99).*
Mogul et al. 2006 (Synthesis and magnetic characterization of microstructures prepared from microbial templates of differing morphology. Materials Letters 60:19-22).*
Tomaselli 1997 (Chapter 1: Morphology, Ultrastructure and Taxonomy of *Arthrospira* (*Spirulina*) *maxima* and *Arthrospira* (*Spirulina*) *platensis* in Vonshak (Ed) 1997; *Spirulina platensis* (*Arthrospira*): Physiology, Cell-biology and Biotechnology, CRC Press, Taylor & Francis Ltd).*
Sotiropoulou et al. 2008 (Biotemplated Nanostructured Materials, Chem. Mater. 20:821-834).*
Lengke et al. 2006 (Morphology of Gold Nanoparticles Synthesized by Filamentous Cyanobacteria from Gold (I)-Thiosulfate and Gold(III)-Chloride Complexes; Langmuir et al. 2006, 22, 2780-2787).*
M. Otsuka, et al.; "Preparation of Metal Microcoils Based on Electroless Plating of Helical Structure in Plant Fibrovascular Bundles;" Polymer Preprints, Japan; vol. 53; No. 1; May 10, 2004; pp. 1094, II Pe009/Cited in International Search Report.
M. Otsuka, et al.; "Preparation and Characterization of Left-handed Electroconductive Microcoils Molded from Helical Structures in Plant Fibrovascular Bundles;" Polymer Preprints, Japan; vol. 53; No. 2; Sep. 1, 2004; pp. 3670-3671, 1J12/Cited in International Search Report.
K. Kamata, et al.; "Shokubutsu Soshiki kara Hidarimaki Kinzoku Microcoil o Sakusei—Ikansoku 'Rasenmon' Template;" Expected Materials for the Future; vol. 8; No. 8; 2008; pp. 2-4/Cited in International Search Report.

(Continued)

*Primary Examiner* — Gary Nickol
*Assistant Examiner* — Mary Lyons
(74) *Attorney, Agent, or Firm* — Kratz, Quintos & Hanson, LLP

(57) ABSTRACT

A helical fine structure of the present invention is characterized by including: a phytoplankton having a helical shape and selected from a group of cyanobacteria called *Spirulina*; and a surface modification layer formed on the phytoplankton. The surface modification layer includes at least one metal plating layer. Thereby, the helical fine structure can be utilized as an electric-wave shield or an absorber. Moreover, a method for producing the helical fine structure is characterized in that a prestep of a step of forming the surface modification layer on the phytoplankton having a helical shape includes a washing step with an organic solvent to remove an outer membrane from a surface of the phytoplankton.

5 Claims, No Drawings

(56) References Cited

OTHER PUBLICATIONS

N. Matsunaga, et al.; "A Study of the Fragmentation of Spiral Trichome of Blue-green Algae '*Spirulina platensis*' by Freeze-thawing Methods;" The Journal of Japanese Society for Cryobiology and Cryotechnology; vol. 40; No. 2; 1994; pp. 56-62/Cited in International Search Report.

Y. Hosoyamada, et al.; "Effects of Water soluble and insoluble Fractions of *Spirulina* on Glucose unabsorption in Rats;" Bulletin of Chiba College of Health Science; vol. 10; No. 1; 1991; pp. 27-30/ Cited in International Search Report.

International Search Report for International Application No. PCT/JP2010/057306 dated Jun. 23, 2010.

Full English translation of this document listed in IDS filed Sep. 29, 2011: K. Kamata, et al.; "Shokubutsu Soshiki Kara Hidarimaki Kinzoku Microcoil o Sakusei—Ikansoku 'Rasenmon' Template;" Expected Materials for the Future; vol. 8; No. 8; 2008; pp. 2-4/cited in International Search Report.

Full English translation of this document listed in IDS filed Sep. 29, 2011: Y. Hosoyamada, et al.; "Effects of Water soluble and insoluble Fractions of *Spirulina* on Glucose unabsorption in Rats;" Bulletin of Chiba College of Health Science; vol. 10; No. 1; 1991; pp. 27-30/ cited in International Search Report.

\* cited by examiner

HELICAL FINE STRUCTURE, METHOD FOR PRODUCING THE SAME, AND ELECTRIC-WAVE SHIELD OR ABSORBER USING THE HELICAL FINE STRUCTURE

TECHNICAL FIELD

The present invention relates to a fine structure having a helical shape, and particularly relates to a helical fine structure applicable to an electric-wave (a radio-wave) shield or absorbing material.

BACKGROUND ART

In order to make observation with an electron microscope easy by preventing electrification due to irradiation of an electron beam, generally, a conductive film has been heretofore formed on the surface of a microorganism sample or the like having no conductivity. This practice serves as a motivation for forming a conductive film on a tissue surface of a microorganism for industrial application. However, the practice does not necessarily suggest specifically on what parts of what microorganism species, and for what applications, its benefits can be obtained by forming the conductive film.

Meanwhile, regarding an application of a conductive structure having a helical shape as an electric-wave (a radio-wave) shield or an absorber, JP-A 2000-027072 (Patent Document 1) discloses an example in which a helical carbon deposit formed by a vapor deposition method is utilized as an electric-wave shield or an absorber. However, the shape of the carbon deposit formed by the vapor deposition method varies due to influences of the concentration of a raw-material gas in a reactor or on a substrate, the composition of the raw-material gas, the temperature distribution, and the like. It is extremely difficult to efficiently grow a deposit having an orderly helical shape.

To avoid such instability of the vapor deposition method, JP-A 2009-221149 (Patent Document 2) discloses a method in which a piece of a vessel secondary wall having a helical shape is taken out from a vascular plant, and a conductive film is formed on the surface thereof for use as an electric-wave shield or an absorber. However, in the process of taking out the piece of the vessel secondary wall having a helical shape from the vascular plant, since an unnecessary portion around the piece has to be removed by a large amount, the raw material efficiency is low. In addition, to remove the unnecessary portion, a large amount of chemicals has to be introduced, and long processing time is required. For this reason, a more efficient production method has been demanded.

DISCLOSURE OF THE INVENTION

The present invention has been made by focusing on such problems. An object of the present invention is to provide a helical fine structure capable of efficient mass production.

In this connection, the present inventors have made studies on the material suitable for a helical fine structure capable of mass production. As a result, the inventors have found an approach employing a phytoplankton which does not particularly require removal of an unnecessary portion therefrom.

Specifically, the helical fine structure according to the present invention is characterized by including: a phytoplankton having a helical shape; and a surface modification layer formed on the phytoplankton. Moreover, the helical fine structure is characterized in that the surface modification layer includes at least one metal plating layer. Note that the phytoplankton on which the surface modification layer is formed may be in any state with an outer membrane remained on a surface thereof and thus unremoved therefrom, or with the outer membrane being removed. Further, the helical fine structure is characterized in that the phytoplankton having a helical shape is a phytoplankton selected from the group of cyanobacteria called *Spirulina* and including *Arthrospira Platensis*, *Arthrospira Maxima*, and *Arthrospira Subsalsa* belonging to *Arthrospira* genus.

Next, a method for producing the helical fine structure is characterized in that a prestep of a step of forming the surface modification layer on the phytoplankton having a helical shape includes a step of removing the outer membrane from the surface of the phytoplankton. Moreover, the method for producing the helical fine structure is characterized in that the step of removing the outer membrane from the surface of the phytoplankton is a washing step with an organic solvent. Further, the method for producing the helical fine structure is characterized by including: a drying step of drying the phytoplankton having a helical shape to obtain a deformed dried phytoplankton; and a shape recovering step of permeating the dried phytoplankton with a polar solvent to cause the phytoplankton to recover the same helical shape as before the drying step.

Furthermore, an electric-wave shield or an absorber according to the present invention is characterized by including multiple helical fine structures in each of which a surface modification layer including at least one metal plating layer is formed on a phytoplankton having a helical shape, the helical fine structures electrically or magnetically connected together to form an assembly.

As described above, the helical fine structure of the present invention includes the phytoplankton having a helical shape on which the surface modification layer is formed. Moreover, unlike a vascular plant described in the previous section, the phytoplankton employed in the helical fine structure of the present invention is a material which does not particularly require removal of an unnecessary portion therefrom. Accordingly, efficient production is possible. Further, the surface modification layer including at least one metal plating layer produces an effect that the helical fine structure can be utilized as an electric-wave shield or an absorber.

BEST MODES FOR PRACTICING THE INVENTION

Embodiments of the present invention are described below in detail.

In the present invention, a helical fine structure usable for various applications is obtained by forming a surface modification layer on a phytoplankton having a helical shape. Examples of the species of the phytoplankton used as the raw material include the group of cyanobacteria generally called *Spirulina* and consisting of *Arthrospira Platensis*, *Arthrospira Maxima*, and *Arthrospira Subsalsa* belonging to the genus *Arthrospira*. The number of turns in the helix during the growth of a *Spirulina* individual is 5 to 10. The typical dimensions of *Spirulina* are: 300 to 500 µm in length measured in the axial direction and approximately 50 µm in diameter.

As the surface modification layer, a conductive layer is formed by metal plating, for example. Thus, a microcoil that is a small electrical element is formed. In a case where a conductive microcoil having the same typical dimension values as described above is formed, the self-resonant frequency of the single microcoil formed with a stray capacitance is in the region of 100 GHz to 1 THz. Thus, the microcoil can be used as an electric-wave shield or an absorber having a resonance absorption function with respect to an electromagnetic wave in this region.

Moreover, if the microcoil is brought into contact with and electrically connected to a microcoil of the same type, both equivalent coil length and parasitic capacitance are increased. Thus, the resonant frequency range can be extended to a lower frequency region. To surely connect the microcoils electrically, the plating film should be formed in a condition where multiples of *Spirulina* are connected to each other.

For example, by immersing a group of *Spirulina* in ethyl alcohol, the condition where the multiples of *Spirulina* are connected to each other can be obtained. When an outer membrane of *Spirulina* is disintegrated and removed with ethyl alcohol, a matter thus disintegrated and removed and an effluent from the cell form a mucus-like substance that helps a large number of *Spirulina* to aggregate therearound. By subjecting this aggregate to a plating treatment, the microcoils connected to each other can be produced.

As another means for electrically connecting the microcoils, there is a method in which an external magnetic field is applied to magnetized microcoils so that the microcoils can be connected to each other. A group of *Spirulina* is prepared in which a magnetized layer such as a Ni plating layer is formed on the surface of each of the *Spirulina* individuals. Then, the group is assembled with fibers such as, for example, pulp, while an external magnetic field is being applied thereto. Thereby, a network of microcoils connected to each other can be mixed within the pulp fibers. By molding this assembly into a sheet form followed by drying, a papery electric-wave shield or absorber can be produced.

Note that the microcoils do not necessarily have to be connected to each other in a state of conductive contact in a strict sense. If the multiple microcoils are close to each other at a small distance, the microcoils are magnetically connected to each other by mutual inductance, and an extended line is formed. This can produce an effect that the resonant frequency range is extended to a lower region. For example, if a powder of the microcoil is dispersed in a thermosetting epoxy resin, this product can be used as an ink paste. A film coated with this paste and cured by heating works as an electric-wave shield or an absorber having favorable loss characteristics in the frequency region of, for example, 1 to 10 GHz.

Further, in order to extend the frequency range to a lower frequency region, it is effective to dispose a high dielectric material around the coil. For example, a film made of a ferroelectric material may be formed on the surface of each coil. In a case of the aforementioned papery electric-wave shield or absorber, the film made of a ferroelectric material may be formed on the mixed fiber.

Meanwhile, in the conventional usage of *Spirulina*, such as food, feed, and raw material of a pigment, harvested *Spirulina* is pulverized by dry-crushing, or molded into an aggregate in a pellet form, for example. In this processing, the helical shape of the *Spirulina* individuals is destroyed. This is because the target in the conventional usage of *Spirulina* is mostly the components of its content. Accordingly, the importance of retaining the helical shape of the *Spirulina* individuals is not recognized in the processing into the dried form suitable for measurement, transportation, and storage.

*Spirulina* loses its helical shape as deformed by drying without pulverizing or pelletizing. Normally, *Spirulina* floats in a culture liquid or the like and keeps its helical shape. However, when surrounding water is removed, *Spirulina* is squashed due to deformation by its own weight and then dried into a planar zigzag shape. Thus, in the usage of *Spirulina* according to the present invention, it is quite useful to obtain *Spirulina* in a dry form which is suitable for measurement, transportation, and storage, and which still enables the helical shape to be retained.

In this connection, the present inventors have made earnest experiments to reveal the characteristics of *Spirulina* and its dried product. As a result, the inventors have found out that even if *Spirulina* is squashed due to deformation by its own weight and dried in a planar zigzag shape, imbibition with a polar solvent such as water and alcohols permeable into a hydrophilic tissue of dried *Spirulina* allows recovering of the dimensional helical shape. This eliminates the need to dry and keep the helical shape by a method such as freeze-drying that requires a dedicated device. Thus, the processing can be performed inexpensively in large amounts using a simple device.

In addition, the present inventors have found out that when *Spirulina* is dried, a crack is formed into a cell wall of *Spirulina*. Through this crack, liquids such as water and alcohols used in the subsequent shape recovering step can readily permeate a tissue of dried *Spirulina*. Effective components including nutrients such as various amino acids, pigments such as chlorophyll, phycocyanin and carotenoid, and the like are efficiently extracted into these liquids. This makes effective utilization of the resources possible.

Note that in the aforementioned step of disintegrating and removing the outer membrane of *Spirulina* with ethyl alcohol also, the effective components including nutrients, pigments, and the like are extracted into ethyl alcohol. Moreover, exactly the same shape recovery as described above is exhibited also in a case of drying *Spirulina* from which the outer membrane has been removed. Thus, remaining effective components can be further extracted in the shape recovering step.

The present invention will be described below in detail based on Examples. Note that in Examples illustrated below, *Arthrospira Platensis* was selected as the *Spirulina* species.

Example 1

In order to eliminate a problem arising from various kinds of ions remaining in a culture liquid in the subsequent step, filter-washing was performed using running water while *Spirulina* was being held by a mesh filter having an opening size of 25 μm or smaller. Then, *Spirulina* was introduced into ethyl alcohol to remove an outer membrane thereof. The mucosa-like outer membrane lysates were assembled to form a large number of floating pieces, and portions of the cytoplasm and pigments were eluted into ethyl alcohol. The solution containing the mixture of these was passed through a coarse mesh filter having an opening size of 250 μm or larger. *Spirulina* was passed therethrough, while the cytoplasm and the outer membrane lysates were trapped. Ethyl alcohol containing *Spirulina* thus passed was separated from ethanol containing the pigment component with a fine mesh filter having an opening size of 25 μm or smaller. Thereby, *Spirulina* was trapped.

Ni plating was performed on trapped Spirulina according to the following procedure.

MELTEX® and MELPLATE® are trademarks. The generic term of MELPLATE® is "Ni plating solution." First, *Spirulina* was introduced into an aqueous solution containing a catalyst (manufactured by Meltex Inc, product name: Melplate activator 7331). The catalyst was attached to *Spirulina* floating in the solution. Then, the mixture was introduced into a Ni plating solution (manufactured by Meltex Inc, product name: Melplate NI-871), and electroless Ni plating (i.e., modification treatment including coating treatment) was performed while the *Spirulina* was again floating in the solution. The thickness of the Ni plating layer was approximately 1 μm.

According to the procedure described above, a conductive helical fine structure having an average diameter of approximately 0.05 mm and an average length of approximately 0.5 mm was obtained.

Example 2

In order to eliminate a problem arising from various kinds of ions remaining in a culture liquid in the subsequent steps, filter-washing was performed using running water while *Spirulina* was being held by a mesh filter having an opening size of 25 μm or smaller. Then, *Spirulina* was introduced into ethyl alcohol to remove an outer membrane thereof. The multiple *Spirulina* individuals were connected to each other with the mucosa-like outer membrane lysates to form a *Spirulina* assembly. In addition, portions of the cytoplasm and pigments were eluted into ethyl alcohol. The solution containing the mixture of these was passed through a fine mesh filter having an opening size of 25 μm or smaller, and separated from ethanol containing the pigment component. Thereby, the *Spirulina* assembly was trapped.

Ni plating was performed on the trapped *Spirulina* assembly according to the following procedure.

First, the *Spirulina* assembly was introduced into an aqueous solution containing a catalyst (manufactured by Meltex Inc, product name: Melplate activator 7331). The catalyst was attached to the *Spirulina* assembly floating in the solution. Then, the mixture was introduced into a Ni plating solution (manufactured by Meltex Inc, product name: Melplate NI-871), and electroless Ni plating (i.e., modification treatment including coating treatment) was performed while the *Spirulina* assembly was again floating in the solution. The thickness of the Ni plating layer was approximately 1 μm. According to the procedure described above, a microcoil assembly was obtained which was an aggregate of multiple microcoils each having dimensions: an average diameter of approximately 0.05 mm and an average length of approximately 0.5 mm.

Example 3

In order to eliminate a problem arising from various kinds of ions remaining in a culture liquid in the subsequent steps, filter-washing was performed using running water while *Spirulina* was being held by a mesh filter having an opening size of 25 μm or smaller. Then, *Spirulina* was introduced into ethyl alcohol to remove an outer membrane thereof. The mucosa-like outer membrane lysates were assembled to form a large number of floating pieces, and portions of the cytoplasm and pigments were eluted into ethyl alcohol. The solution containing the mixture of these was passed through a coarse mesh filter having an opening size of 250 μm or larger. *Spirulina* was passed therethrough, while the cytoplasm and the outer membrane lysates were trapped. Ethyl alcohol containing *Spirulina* thus passed was separated from ethanol containing the pigment component with a fine mesh filter having an opening size of 25 μm or smaller. Thereby, *Spirulina* was trapped.

The trapped *Spirulina* individuals were dried with hot air to obtain dried *Spirulina* suitable for measurement, transportation, and storage. The dried *Spirulina* thus obtained was introduced into water, and thereby the helical shape was recovered. The Ni plating was possible according to the same procedure as those in Examples 1, 2.

Example 4

The microcoil assembly obtained in Example 2 was mixed with a paper pulp, and molded into a sheet form followed by drying. Thus, an electric-wave shield or absorbing paper having a favorable attenuation rate of 20 dB or higher in the frequency band of 1 to 10 GHz was obtained.

Possibility of Industrial Application

A helical fine structure according to the present invention includes a phytoplankton having a helical shape and a surface modification layer formed on the phytoplankton, and is capable of efficient mass production. The surface modification layer includes at least one metal plating layer. Thereby, the helical fine structure has a possibility of industrial applicability that it is utilized as an electric-wave shield or an absorbing material.

The invention claimed is:

1. A method for producing a helical fine structure characterized by comprising the steps of:
    filter-washing a phytoplankton. using running water while holding the phytoplankton by a mesh filter having an opening size of 25 μm or smaller, wherein the phytoplankton has a helical shape, wherein the phytoplankton having a helical shape is a phytoplankton selected from the group of cyanobacteria called *Spirulina* and consisting of *Arthrospira Platensis, Arthrospira Maxima*, and *Arthrospira Subsalsa* belonging to *Arthrospira* genus;
    removing an outer membrane from a surface of the filter-washed phytoplankton by introducing the phytoplankton into an ethyl alcohol solution;
    passing the ethyl alcohol solution though a coarse mesh filter having an opening size of 250 μm or larger, wherein the ethyl alcohol solution contains the phytoplankton, floating pieces formed from assembled mucosa-like outer membrane lysates, and portions of a cytoplasm and a pigment component eluted into the ethyl alcohol solution, and thereby the floating pieces and the cytoplasm are trapped by the coarse mesh filter, while the ethyl alcohol solution containing the phytoplankton and the pigment is passed therethrough;
    passing the ethyl alcohol solution through a mesh filter having an opening size of 25 μm or smaller to trap the phytoplankton, wherein the ethyl alcohol solution contains the phytoplankton and the pigment and has passed through the coarse mesh filter; and
    forming a surface modification layer on the trapped phytoplankton, wherein the surface modification layer includes at least one metal plating layer.

2. The method for producing a helical fine structure according to claim 1, characterized by comprising:
    a drying step of drying the phytoplankton having a helical shape to obtain a deformed dried phytoplankton; and
    a shape recovering step of permeating the dried phytoplankton with a polar solvent to cause the phytoplankton to recover the same helical shape as before the drying step.

3. A method for producing a helical fine structure characterized by comprising the steps of:
    filter-washing a phytoplankton using running water while holding the phytoplankton by a mesh filter having an opening size of 25 μm or smaller, wherein the phytoplankton has a helical shape, wherein the phytoplankton having a helical shape is a phytoplankton selected from the group of cyanobacteria called *Spirulina* and consisting of *Arthrospira Platensis, Arthrospira maxima*, and *Arthrospira Subsalsa* belonging to *Arthrospira* genus;
    removing an outer membrane from a surface of the filter-washed phytopiankton by introducing the phytoplankton into an ethyl alcohol solution;

passing the ethyl alcohol solution through a mesh filter having an opening size of 25 μm or smaller to trap a phytoplankton assembly connected with mucosa-like outer membrane lysates, wherein the ethyl alcohol solution contains the phytoplankton assembly, and portions of a cytoplasm and a pigment component eluted into the ethyl alcohol solution; and forming a surface modification layer on the trapped phytoplankton assembly, wherein the surface modification layer includes at least one metal plating layer.

4. The method for producing a helical fine structure according to claim 3, characterized by comprising:
 a drying step of drying the phytoplankton having a helical shape to obtain a deformed dried phytoplankton; and
 a shape recovering step of permeating the dried phytoplankton with a polar solvent to cause the phytoplankton to recover the same helical shape as before the drying step.

5. A method for producing an electric-wave shield or an absorber characterized by comprising a plurality of helical fine structures electrically or magnetically connected together to form an assembly, the method characterized by comprising the steps of:
 filter-washing phytoplankton using running water while holding the phytoplankton by a mesh filter having an opening size of 25 μm or smaller, wherein the phytoplankton has a helical shape, wherein the phytoplankton having a helical shape is a phytoplankton selected from the group of cyanobacteria called *Spirulina* and consisting of *Arthrospira Platensis, Arthrospira Maxima*, and *Arthrospira Subsalsa* belonging to *Arthrospira* genus;
 removing an outer membrane from a surface of the filter-washed phytoplankton by introducing the phytolankton into an ethyl alcohol solution;
 passing the ethyl alcohol solution through mesh filter having an opening size of 25 μm or smaller to trap a phytoplankton assembly connected with mucosa-like outer membrane lysates, wherein the ethyl alcohol solution contain the phytoplankton assembly, and portions of a cytoplasm and a pigment component eluted into the ethyl alcohol solution; and
 forming a surface modification layer on the trapped phytoplankton assembly to obtain a microcoil assembly, wherein the surface modification layer includes at least one metal plating layer;
 mixing the microcoil assembly with a paper pulp, and molding the mixture into a sheet form followed by drying to thus obtain an electric-wave shield or an absorber.

* * * * *